(12) United States Patent
Montgomery et al.

(10) Patent No.: US 11,103,510 B2
(45) Date of Patent: Aug. 31, 2021

(54) JAK1 PATHWAY INHIBITORS FOR THE TREATMENT OF CYTOKINE-RELATED DISORDERS

(71) Applicant: Incyte Corporation, Wilmington, DE (US)

(72) Inventors: Michael O'Neill Montgomery, Yardley, PA (US); Ahmad Naim, Hatboro, PA (US); Susan Snodgrass, Greenville, DE (US)

(73) Assignee: Incyte Corporation, Wilmington, DE (US)

( * ) Notice: Subject to any disclaimer, the term of this patent is extended or adjusted under 35 U.S.C. 154(b) by 170 days.

(21) Appl. No.: 16/276,157

(22) Filed: Feb. 14, 2019

(65) Prior Publication Data

US 2019/0255053 A1    Aug. 22, 2019

Related U.S. Application Data

(60) Provisional application No. 62/631,825, filed on Feb. 18, 2018, provisional application No. 62/710,446, filed on Feb. 16, 2018.

(51) Int. Cl.
| | | |
|---|---|---|
| *A61K 31/397* | (2006.01) | |
| *A61K 31/4427* | (2006.01) | |
| *A61K 31/56* | (2006.01) | |
| *A61P 37/00* | (2006.01) | |
| *A61K 31/519* | (2006.01) | |
| *A61P 37/02* | (2006.01) | |
| *A61K 31/4155* | (2006.01) | |
| *A61K 31/573* | (2006.01) | |
| *C07K 16/28* | (2006.01) | |
| *A61K 31/437* | (2006.01) | |

(52) U.S. Cl.
CPC ........ *A61K 31/519* (2013.01); *A61K 31/4155* (2013.01); *A61K 31/437* (2013.01); *A61K 31/573* (2013.01); *A61P 37/00* (2018.01); *A61P 37/02* (2018.01); *C07K 16/2866* (2013.01)

(58) Field of Classification Search
CPC .. A61K 31/397; A61K 31/4427; A61K 31/56; A61P 37/00
USPC .......................... 514/171, 210.2, 210.21, 338
See application file for complete search history.

(56) References Cited

U.S. PATENT DOCUMENTS

| | | |
|---|---|---|
| 7,335,667 B2 | 2/2008 | Rodgers et al. |
| 7,598,257 B2 | 10/2009 | Rodgers et al. |
| 7,834,022 B2 | 11/2010 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,486,902 B2 | 7/2013 | Rodgers et al. |
| 8,513,270 B2 | 8/2013 | Arvanitis et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,765,734 B2 | 7/2014 | Huang et al. |
| 8,933,085 B2 | 1/2015 | Rodgers et al. |
| 8,987,443 B2 | 3/2015 | Liu et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,249,145 B2 | 2/2016 | Rodgers et al. |
| 9,358,229 B2 | 6/2016 | Vannucchi et al. |
| 9,359,358 B2 | 6/2016 | Rodgers et al. |
| 9,382,231 B2 | 7/2016 | Li et al. |
| 9,487,521 B2 | 11/2016 | Zhou et al. |
| 9,498,467 B2 | 11/2016 | Leopold et al. |
| 9,655,854 B2 | 5/2017 | Yeleswaram et al. |
| 9,802,957 B2 | 10/2017 | Zhou et al. |
| 9,993,480 B2 | 6/2018 | Vannucchi et al. |
| 10,166,191 B2 | 1/2019 | Ni et al. |
| 2006/0106020 A1 | 5/2006 | Rodgers et al. |
| 2010/0113416 A1 | 5/2010 | Friedman et al. |
| 2010/0298334 A1 | 11/2010 | Rodgers et al. |
| 2011/0059951 A1 | 3/2011 | Rodgers et al. |
| 2011/0207754 A1 | 8/2011 | Li et al. |
| 2011/0224190 A1 | 9/2011 | Huang et al. |
| 2011/0288107 A1 | 11/2011 | Parikh et al. |
| 2012/0149681 A1 | 6/2012 | Rodgers et al. |
| 2012/0149682 A1 | 6/2012 | Rodgers et al. |
| 2013/0018034 A1 | 1/2013 | Yao et al. |
| 2013/0045963 A1 | 2/2013 | Rodgers et al. |
| 2013/0060026 A1 | 3/2013 | Zhou et al. |
| 2014/0005166 A1 | 1/2014 | Rodgers et al. |
| 2014/0121198 A1 | 5/2014 | Li et al. |

(Continued)

FOREIGN PATENT DOCUMENTS

| | | |
|---|---|---|
| WO | WO 2002/000196 | 1/2002 |
| WO | WO 2017/096331 | 6/2017 |
| WO | WO 2018/013918 | 1/2018 |

OTHER PUBLICATIONS

International Search Report and Written Opinion in International Application No. PCT/US2019/018066, dated Apr. 12, 2019, 12 pages.

(Continued)

*Primary Examiner* — Raymond J Henley, III

(74) *Attorney, Agent, or Firm* — Fish & Richardson P.C.

(57) ABSTRACT

This disclosure relates to JAK1 pathway inhibitors and the use thereof in treating cytokine-related diseases or disorders such as cytokine release syndrome (CRS), hemophagocytic lymphohistiocytosis (HLH), macrophage activation syndrome (MAS), and CAR-T-cell-related encephalopathy syndrome (CRES).

15 Claims, 8 Drawing Sheets

(56) References Cited

U.S. PATENT DOCUMENTS

| | | |
|---|---|---|
| 2014/0256941 A1 | 9/2014 | Liu et al. |
| 2014/0343030 A1 | 11/2014 | Li et al. |
| 2015/0065447 A1 | 3/2015 | Sandor |
| 2015/0065484 A1 | 3/2015 | Yeleswaram et al. |
| 2015/0246046 A1 | 9/2015 | Vaddi |
| 2015/0344497 A1 | 12/2015 | Zhou et al. |
| 2019/0175578 A1 | 6/2019 | Koblish et al. |
| 2019/0233392 A1 | 8/2019 | Wang et al. |
| 2019/0255053 A1 | 8/2019 | Montgomery et al. |
| 2019/0328739 A1 | 10/2019 | Howell et al. |
| 2019/0331697 A1 | 10/2019 | Howell et al. |
| 2020/0063188 A1 | 2/2020 | Howell et al. |

OTHER PUBLICATIONS

International Preliminary Report on Patentability in International Application No. PCT/US2019/018066, dated Aug. 18, 2020, 8 pages.
Aikawa., "Cytokine storm in the pathogenesis of multiple organ dysfunction syndrome associated with surgical insults," Nihon Geka Gakkai Zasshi, Sep. 1996, 97(9):771-777 (English abstract only).
Algre et al., "Hypothermia and hypoglycemia induced by anti-CD3 monoclonal antibody in mice: role of tumor necrosis factor," Eur. J. Immunol., 1990, 20(3):707-710.
Borgia et al., "Features, Treatment, and Outcomes of Macrophage Activation Syndrome in Childhood-Onset Systemic Lupus Erythematosus," Arthritis Rheumatol., 2018, 70(4):616-624.
Brentjens et al., "Treatment of chronic lymphocytic leukemia with genetically targeted autologous T cells: case report of an unforeseen adverse event in a phase I clinical trial," Mol Ther, 2010, 18:666-668.
Bugelski et al., "Monoclonal antibody-induced cytokine-release syndrome," Expert Review of Clinical Immunology, 2009, 5(5):499-521.
Broglie et al., "Ruxolitinib for treatment of refractory hemophagocytic lymphohistiocytosis," blood advances, Aug. 22, 2017, 1(19):1533-1536.
Das et al., "Janus kinase inhibition lessens inflammation and ameliorates disease in murine models of hemophagocytic lymphohistiocytosis," Blood, Jan. 29, 2016, 127(3):1666-1675.
Ferran et al., "Inter-mouse strain differences in the in vivo anti-CD3 induced cytokine release," Clin. Exp. Immunol., 1991, 86(3):537-543.
Ferran et al., "Cytokine-related syndrome following injection of anti-CD3 monoclonal antibody: further evidence for transient in vivo T cell activation," Eur. J. Immunol., 1990, 20(3):509-515.
Flex et al., "Somatically acquired JAK1 mutations in adult acute lymphoblastic leukemia," J Exp Med., 2008, 205(4):751-758.
Fonesca et al., "Interleukin-6 as a key player in systemic inflammation and joint destruction," Autoimmunity Reviews, 2009, 8(7):538-542
Gantner at al., "Concanavalin A-induced T-cell-mediated hepatic injury in mice: the role of tumor necrosis factor," Hepatology, 1995, 21(1):190-198.
Gardner et al., "Decreased Rates of Severe CRS Seen with Early Intervention Strategies for CD19 CAR-T Cell Toxicity Management," ASH 2016, Abstract #586, Dec. 5, 2016, 6 pages.
Guschin et al., "A major role for the protein tyrosine kinase JAK1 in the JAK/STAT signal transduction pathway in response to interleukin-6," Embo J, 1995, 14(7):1421-1429.
Hay et al., "Kinetics and biomarkers of severe cytokine release syndrome after CD19 chimeric antigen receptor-modified T-cell therapy," Immunobio Immunother., Nov. 23, 2017, 130(21):2295-2306.

Juvekar and Ruggeri, "Presentation:Preclinical Efficacy, PD and MoA Studies of Ruxolitinib and Itacitinib in Models of GVHD to Support their Clinical Development," Nov. 29, 2017, 36 pages.
Kenderian et al., "Ruxolitinib Prevents Cytokine Release Syndrome after Car T-Cell Therapy Without Impairing the Anti-Tumor Effect in a Xenograft Model," Abstracts, Biol Blood Marrow Transplant, 2017, 23:S18-S391.
Lee et al., "Current concepts in the diagnosis and management of cytokine release syndrome," Blood, May 29, 2014, 124(2):188-195.
Léo et al., "Identification of a monoclonal antibody specific for a murine T3 polypeptide," Proc. Natl. Acad. Sci. USA, 1987, 34:1374-1378.
Berge et al., "Lists of suitable salts," Journal of Pharmaceutical Science, 66, p. 2 (1977).
"Lists of suitable salts," Remington's Pharmaceutical Sciences, 17th ed., Mack Publishing Company, Easton, Pa., 1985, p. 1418.
Lube et al., "Evans Syndrome at Childhood-Onset Systemic Lupus Erythematosus Diagnosis: A Large Multicenter Study," Pediatr Blood Cancer, 2016, 63:1238-1243.
Mascarenhas, "Primary analysis of a phase II open-label trial of CB039110, a selective JAK1 inhibitor, in patients with myelofibrosis," Haematologica. 2016, pp. 1-22 and Supplemental Data, pp. 1-7.
Maschalidi et al., "Therapeutic effect of JAK1/2 blockade on the manifestations of hemophagocytic lymphoistiocytosis in mice," Blood, May 24, 2016, 128(1):60-71.
Maude et al., "Managing Cytokine Release Syndrome Associated With Novel T Cell-Engaging Therapies," Cancer J., 2014, 20(2):119-122.
Mullighan, "JAK mutations in high-risk childhood acute lymphoblastic leukemia," Proc Natl Acad Sci USA, 2009, 106(23):9414-9418.
Neelapu et al., "Chimeric antigen receptor T-cell therapy—assessment and management of toxicities," Nat Rev Clin Oncol., 2018, 15(1):47-62.
Park et al., "Homogeneous proximity tyrosine kinase assays: scintillation proximity assay versus homogeneous time-resolved fluorescence," Analytical Biochemistry, 1999, 269(1):94-104.
Schram et al., "How I treat hemophagocytic lymphohistiocytosis in the adult patient ," Blood, 2005, 125(19):2908-2914.
Shimizu et al., "Distinct cytokine profile in juvenile systemic lupus erythematosus-associated macrophage activation syndrome,"Clin Immunol., Feb. 2013, 146(2):73-76.
Smolen et al., "Effect of interleukin-6 receptor inhibition with tocilizumab in patients with rheumatoid arthritis (OPTION study): a double-blind, placebo-controlled, randomised trial," Lancet, 2008, 371:987-997.
Snodgrass et al., "Cytokine Release Syndrome: CD19-directed CAR T cell therapy, Bispecifics & Haploidentical HSCT," Nov. 22, 2017, 33 pages.
Taylor et al., "The JAK1-Selective Inhibitor Filgotinib Displays an Anti-Inflammatory Biomarker Signature in Rheumatoid Arthritis Patients," 2016 ACR/ARHP Annual Meeting, Abstract No. 2616, Sep. 28, 2016.
Teachey et al., "Identification of Predictive Biomarkers for Cytokine Release Syndrome after Chimeric Antigen Receptor T cell Therapy for Acute Lymphoblastic Leukemia," Cancer Discov. 6, 664-679 (2016).
Tisoncik et al., "Into the Eye of the Cytokine Storm," Microbiology and Molecular Biology Reviews, Mar. 2012, 76(1):16-32.
www.quora.com, "What is a 'cytokine storm,' and what are the diseases that cause that?", retrieved on Feb. 18, 2018, retrieved from URL <https://www.quora.com/What-is-a-cytokine-storm-and-what-are-the-diseases-that-cause-that>, 9 pages.
Xu et al., "Cytokine release syndrome in cancer Immunotherapy with chimeric antigen receptor engineered T cells," Cancer Lett., 2014, 343(2):172-178.
Zhang et al., "An analytical biomarker for treatment of patients with recurrent B-ALL after remission induced by infusion of anti-CD19 chimeric antigen receptor T (CAR-T) cells," Sci China Life Sci., Apr. 2016, 59(4):379-385.
Science IP Search Report, dated Mar. 2021, 421 pages.

JAK1 PATHWAY INHIBITORS FOR THE TREATMENT OF CYTOKINE-RELATED DISORDERS

TECHNICAL FIELD

This disclosure relates to JAK1 pathway inhibitors and the use thereof in treating cytokine-related diseases or disorders.

BACKGROUND

Cytokine-related diseases or disorders are characterized by excessive immune activation and include cytokine release syndrome (CRS), hemophagocytic lymphohistiocytosis (HLH), macrophage activation syndrome (MAS), and CAR-T-cell-related encephalopathy syndrome (CRES).

Cytokine release syndrome (CRS) is a direct result of overproduction of inflammatory cytokines caused by supraphysiological levels of immune activation and is manifested as a clinical constellation of symptoms including fever, nausea, fatigue, myalgia, malaise, hypotension, hypoxia, capillary leak, resulting in potential multi-organ toxicity.

CRS is an unwanted side effect of, e.g., immune-based therapies for serious disease states such as cancer. Immune-based therapies that can result in CRS include administration of monoclonal antibodies (mAbs) and, more recently, adoptive T-cell therapies for cancer. Lee et al. *Blood.* 2014, 124(2): 188-195. For example, chimeric antigen receptor (CAR) T-cell therapy uses altered T-cells to target cancers and is already approved by the FDA for use in certain forms of refractory non-Hodgkin lymphoma and pediatric relapsed lymphoblastic leukemia (ALL).

The cytokine profiles involved in CRS encompass two main cellular sources: T lymphocyte derived cytokines including interferon-gamma (IFN)-γ, IL-2, IL-6, soluble IL-6 receptor (IL-6R) and granulocyte-macrophage colony stimulating factor (GM-CSF); and cytokines mainly secreted by the monocytes and/or macrophages such as IL-1β, IL-6, IL-12, IL-18, and tumor necrosis factor (TNF)-α. Xu X J, Tang Y M. *Cancer Lett.* 2014; 343:172-8. Zhang Y., et al. *Sci China Life Sci.* 2016; 59:379-85. Brentjens R., et al. *Mol Ther.* 2010; 18:666-8.

Modulation of the exaggerated cytokine response resulting in CRS has the potential to provide significant clinical benefit. For example, tocilizumab, an antibody against the IL-6 receptor (IL-6R), decreases the rates of severe CRS and is FDA approved for use in CRS. However, tocilizumab's mechanism of action is restricted to anti-IL-6R only.

Hemophagocytic lymphohistiocytosis (HLH), another syndrome of excessive or uncontrolled immune activation, occurs mostly in infants from birth to 18 months of age, but can also occur in adults. HLH can be primary (familial) or secondary, meaning it occurs in the setting of other infectious, malignant, rheumatologic, or metabolic conditions. Symptoms of HLH include cytopenias, hepatosphlenomegaly, and fevers. Schram, A. and Berliner, N. *Blood.* 2005. 125(19), 2908-2914.

Macrophage activation syndrome (MAS) is clinically presented in a manner similar to HLH (and even considered a secondary or acquired for of HLH) and is an episode of increased inflammation associated with infection, rheumatic disease, or malignancy. Borgia, R. E. et al. *Arthritis Rheumatol.,* 2018, doi: 10.1002/art.40417, pre-publication. MAS was initially described as associated with juvenile idiopathic arthritis, but is also a increasingly recognized as a complication of other diseases such as childhood-onset systemic lupus erythematosus (cSLE). Shimizu M., et al. *Clin Immunol.* 2013 February; 146(2):73-6. The development of MAS is characterized by a substantial increase in numerous pro-inflammatory cytokines, i.e., a cytokine storm. Borgia, R. E. et al. *Arthritis Rheumatol.,* 2018, doi: 10.1002/art.40417, pre-publication. MAS is a life-threatening condition with high mortality rates: 8-22% in pediatric autoimmune diseases generally and 10-22% in MAS complicating cSLE. Borgia, R. E. et al. *Arthritis Rheumatol.,* 2018, doi: 10.1002/art.40417, pre-publication.

CAR-T-cell related encephalopathy syndrome (CRES) is the second most common adverse event, after CRS, associated with CAR-T-cell therapy. CRES is typically characterized by a toxic encephalopathy state with symptoms of confusion and delirium and occasional seizures and cerebral edema. The manifestation of CRES can be biphasic with symptoms occurring within the first 5 days and/or 3-4 weeks after cellular immunotherapy. The pathophysiological mechanism is believed to involve passive diffusion of cytokines into the brain of patients treated with CAR-T-cell therapy. The reduction or elimination of this mechanism can be beneficial to such patients. Neelapu, et al. *Nat Rev Clin Oncol.* 2018, 15(1) 47-62.

Accordingly, there is a need to develop new therapies for the treatment of cytokine-related diseases or disorders. This application addresses this need and others.

DESCRIPTION OF THE DRAWINGS

FIG. 2A shows the inhibition of IL-6. FIG. 2B shows the inhibition of IFNγ. FIG. 2C shows the inhibition of GM-CSF.

FIG. 3A shows the inhibition of IL-12. FIG. 3B shows the inhibition of IL-1β. FIG. 3C shows the inhibition of IL-18.

SUMMARY

Provided herein are methods for the treatment of a cytokine-related disease or disorder in a subject in need thereof, comprising administering to said patient a therapeutically effective amount of a JAK1 pathway inhibitor, or a pharmaceutically acceptable salt thereof.

Provided herein is a JAK1 pathway inhibitor, or a pharmaceutically acceptable salt thereof, for the treatment of a cytokine-related disease or disorder in a subject in need thereof.

Provided herein is a use of a JAK1 pathway inhibitor, or a pharmaceutically acceptable salt thereof, for manufacture of a medicament for use in treating a cytokine-related disease or disorder in a subject in need thereof.

DETAILED DESCRIPTION

The present invention provides, inter alia, a method of treating a cytokine-related disease or disorder in a subject in need thereof, comprising administering to said subject a therapeutically effective amount of a JAK1 pathway inhibitor, or a pharmaceutically acceptable salt thereof.

The methods described herein utilize JAK1 pathway inhibitors, particularly JAK1 selective inhibitors. A JAK1 selective inhibitor is a compound that inhibits JAK1 activity preferentially over other Janus kinases. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, et al., *Autoimmunity Reviews*, 8:538-42, 2009). Because IL-6 signals, at least in part, through JAK1, IL-6 can be indirectly through JAK1 inhibition, resulting in potential clinical benefit (Guschin, et al. *Embo J* 14:1421, 1995; Smolen, et al. *Lancet* 371:987, 2008). Moreover, in some cancers JAK1 is mutated resulting in constitutive undesirable tumor cell growth and survival (Mullighan, *Proc Natl Acad Sci USA*. 106:9414-8, 2009; Flex, *J Exp Med*. 205:751-8, 2008). In other autoimmune diseases and cancers, elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Figure 4:
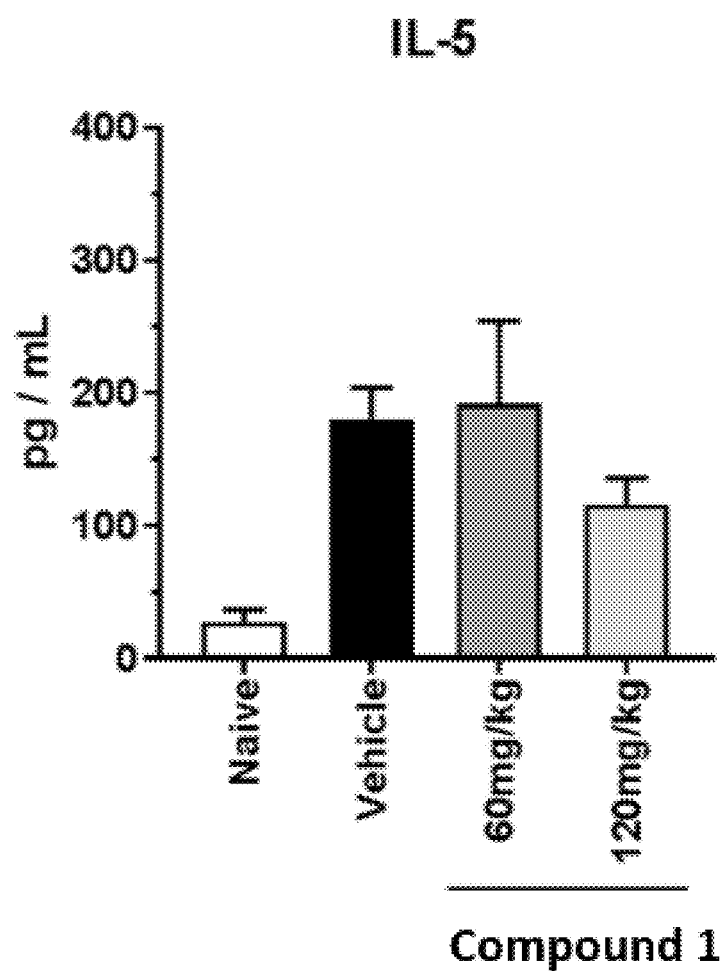
FIG. 4 shows that cytokine IL-5 is unaffected by Compound 1 treatment during concanavalin A induced cytokine release syndrome (see Example C).

A JAK1 pathway inhibitor, specifically Compound 1 (i.e., {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, see Table 1), achieves highly effective dose-dependent modulation of CRS-relevant inflammatory cytokines (see, e.g., Examples B and C, and FIGS. 1, 2A-2C, and 3A-3C). Surprisingly, the therapeutic profile encompasses multiple pathogenic cytokines and is not restricted to IL-6/IL-6R axis only (unlike, e.g., tocilizumab). Efficacy is achieved by inhibiting cytokines derived from T-cells and monocyte/macrophages with high clinical relevance to CRS pathogenesis. Further, the data presented herein in connection with JAK1 inhibitor Compound 1 shows that treatment benefit is achieved without broad cytokine immunosuppression (as demonstrated by unchanged IL-5 levels) (FIG. 4).

In some embodiments, the cytokine-related disease or disorder is cytokine release syndrome (CRS), hemophagocytic lymphohistiocytosis (HLH), macrophage activation syndrome (MAS), or CAR-T-cell-related encephalopathy syndrome (CRES).

In some embodiments, the cytokine-related disease or disorder is cytokine release syndrome (CRS).

In some embodiments, the cytokine-related disease or disorder is hemophagocytic lymphohistiocytosis (HLH).

In some embodiments, the cytokine-related disease or disorder is macrophage activation syndrome (MAS). In some embodiments, the macrophage activation syndrome is associated with systemic juvenile idiopathic arthritis. In some embodiments, the macrophage activation syndrome is associated with pediatric systemic lupus erythematosus.

In some embodiments, the cytokine-related disease or disorder is CAR-T-cell-related encephalopathy syndrome (CRES).

In some embodiments, the present application provides a method of treating cytokine release syndrome in a subject, comprising administering a CAR-T cell therapy to said subject and a JAK1 pathway inhibitor, or a pharmaceutically acceptable salt thereof. In some embodiments, treating is ameliorating or inhibiting. In some embodiments, treating is preventing.

In some embodiments, the JAK1 pathway inhibitor, or a pharmaceutically acceptable salt thereof, is administered simultaneously with the CAR-T cell therapy.

In some embodiments, the JAK1 pathway inhibitor, or a pharmaceutically acceptable salt thereof, is administered after the administration of the CAR-T cell therapy.

In some embodiments, the CAR-T cell therapy is axicabtagene ciloleucel.

In some embodiments, the CAR-T cell therapy is tisagenlecleucel.

In some embodiments, the subject suffers from a B-cell malignancy.

In some embodiments, the subject suffers from diffuse large B-cell lymphoma (DLBCL), primary mediastinal large B-cell lymphoma, high-grade B-cell lymphoma, transformed follicular lymphoma, or acute lymphoblastic leukemia.

In some embodiments, the JAK1 pathway inhibitor, or a pharmaceutically acceptable salt thereof, is selective for JAK1 over JAK2, JAK3, and TYK2 (i.e., a JAK1 selective inhibitor). For example, the compounds described herein, or pharmaceutically acceptable salts thereof, preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio >1). In some embodiments, the compounds or salts are about 10-fold more selective for JAK1 over JAK2. In some embodiments, the compounds or salts are about 3-fold, about 5-fold, about 10-fold, about 15-fold, or about 20-fold more selective for JAK1 over JAK2 as calculated by measuring $IC_{50}$ at 1 mM ATP (e.g., see Example A).

In some embodiments, the JAK1 pathway inhibitor is a compound of Table 1, or a pharmaceutically acceptable salt thereof. The compounds in Table 1 are selective JAK1 inhibitors (selective over JAK2, JAK3, and TYK2). The $IC_{50}$ values obtained by the method of Example A at 1 mM ATP are shown in Table 1.

TABLE 1

| Comp. No. | Prep. | Name | Structure | JAK1 IC$_{50}$ (nM) | JAK2/ JAK1 |
|---|---|---|---|---|---|
| 1 | US 2011/ 0224190 (Example 1) | {1-{1-[3-Fluoro-2-(trifluoromethyl) isonicotinoyl] piperidin-4-yl}-3-[4-(7H-pyrrolo[2,3-d]pyrimidin-4-yl)-1H-pyrazol-1-yl]azetidin-3-yl}acetonitrile | 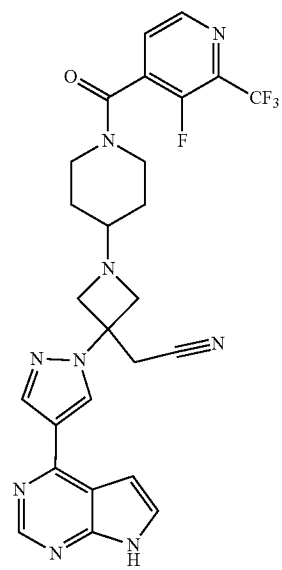 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl) phenyl] piperidine-1-carboxamide | 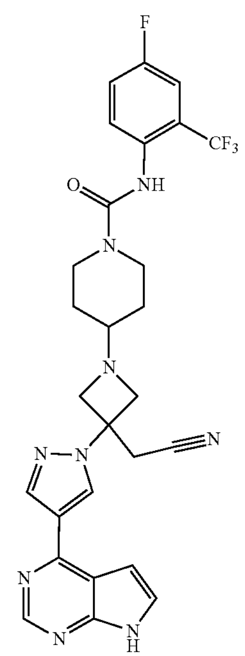 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 3 | US 2011/ 0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 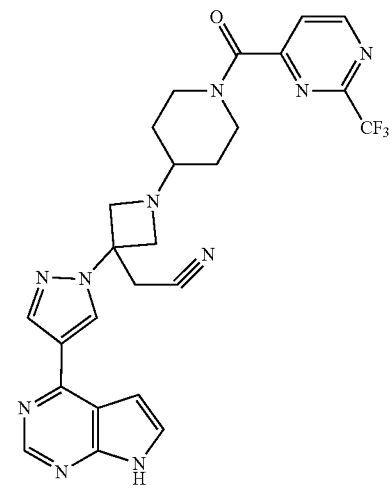 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/ 0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 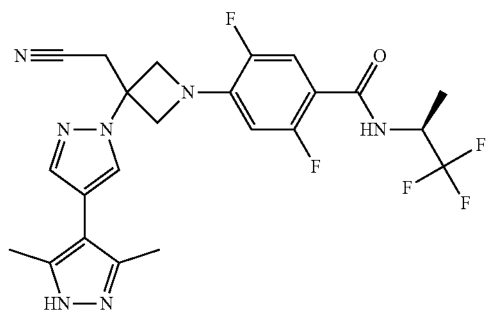 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | US 2014/ 0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 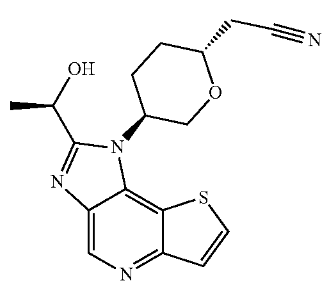 [SMILES: C[C@@H](O)c1nc2cnc3ccsc3c2n1[C@H]1CC[C@H](CC#N)OC1] | ++ | >10 |
| 6 | US 2010/ 0298334 (Example 2)[a] | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 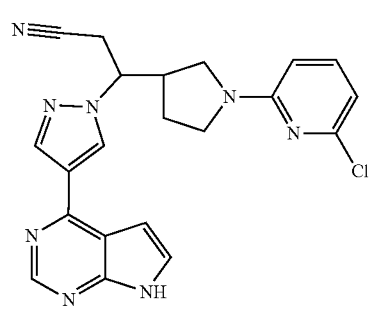 [SMILES: N#CCC(C1CCN(c2cccc(Cl)n2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/JAK1 |
|---|---|---|---|---|---|
| 7 | US 2010/ 0298334 (Example 13c) | 3-(1-[1,3] oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 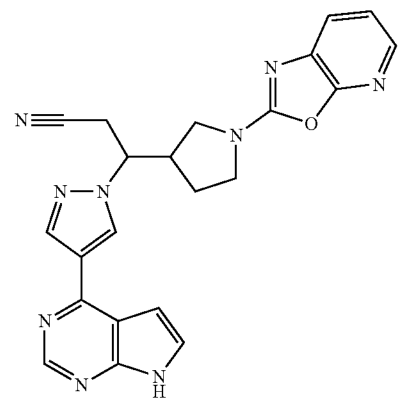 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 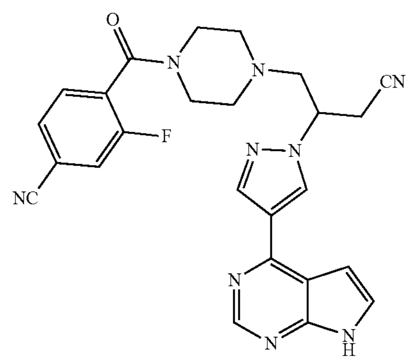 [SMILES: N#CCC(CN1CCN(C(=O)c2ccc(C#N)cc2F)CC1)n1cc(-c2ncnc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 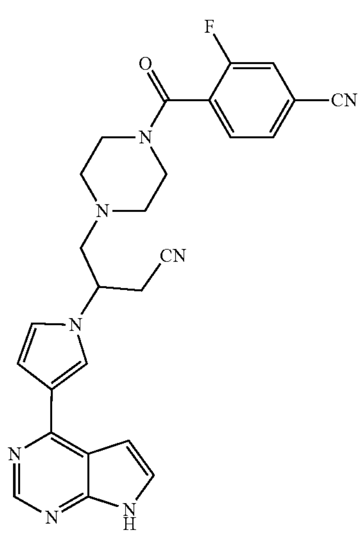 [SMILES: N#CCC(CN1CCN(C(=O)c2ccc(C#N)cc2F)CC1)n1ccc(-c2ncnc3[nH]ccc23)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 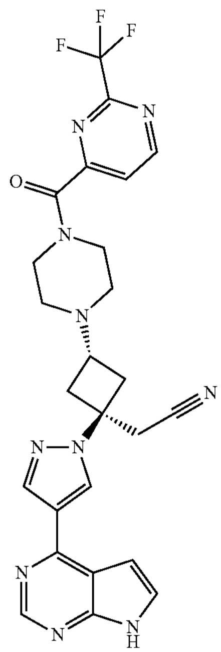 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 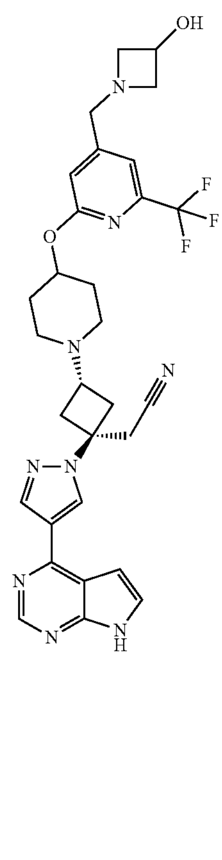 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 12 | US 2012/ 0149681 (Example 161) | {trans-3-(4-{[4-{[(2S)-2-(hydroxymethyl) pyrrolidin-1-yl]methyl}-6-(trifluoromethyl) pyridin-2-yl] oxy}piperidin-1-yl)-1-[4-(7H-pyrrolo[2,3-d]pyrimidin-4-yl)-1H-pyrazol-1-yl]cyclobutyl} acetonitrile | 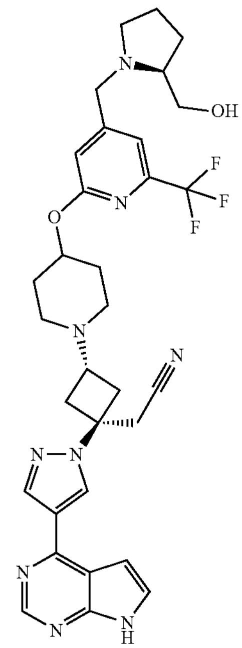 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl) pyrrolidin-1-yl]methyl}-6-(trifluoromethyl) pyridin-2-yl] oxy}piperidin-1-yl)-1-[4-(7H-pyrrolo[2,3-d]pyrimidin-4-yl)-1H-pyrazol-1-yl]cyclobutyl} acetonitrile | 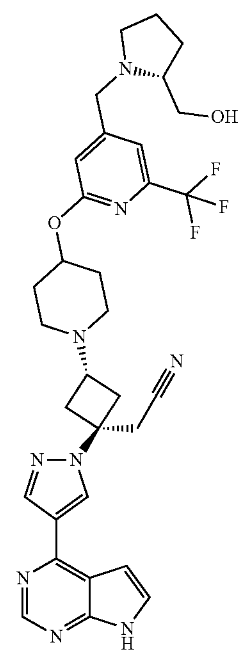 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/ 0149682 (Example 20)[b] | 4-(4-{3-[(dimethylamino) methyl]-5-fluorophenoxy} piperidin-1-yl)-3-[4-(7H-pyrrolo [2,3-d]pyrimidin-4-yl)-1H-pyrazol-1-yl]butanenitrile | 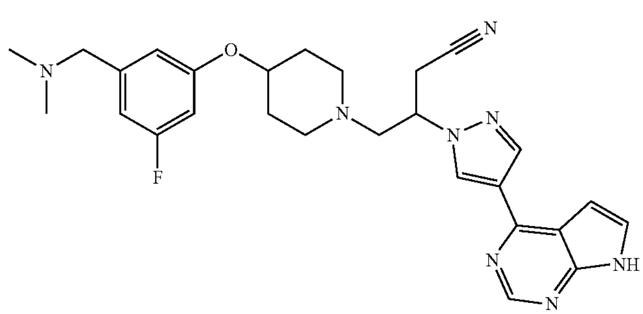 [SMILES: CN(C)Cc1cc(F)cc(OC2CCN(CC(CC#N)n3cc(-c4ncnc5[nH]ccc45)cn3)CC2)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 15 | US 2013/ 0018034 (Example 18) | 5-{3-(cyanomethyl)-3-[4-(7H-pyrrolo[2,3-d]pyrimidin-4-yl)-1H-pyrazol-1-yl] azetidin-1-yl}-N-isopropylpyrazine-2-carboxamide | 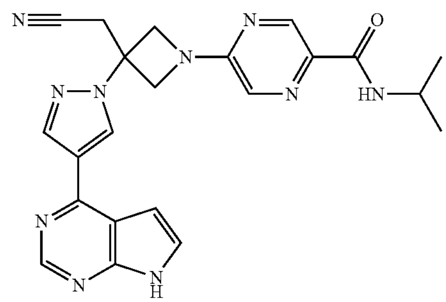 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl] benzamide | 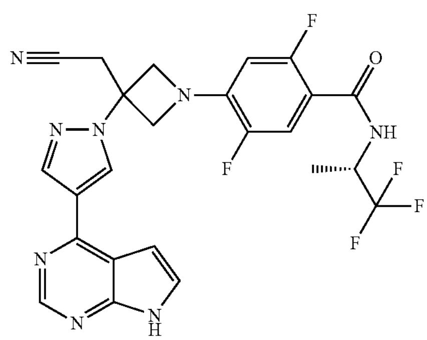 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b] pyridin-4-yl)-1H-pyrazol-1-yl] azetidin-1-yl}-N-isopropylpyrazine-2-carboxamide | 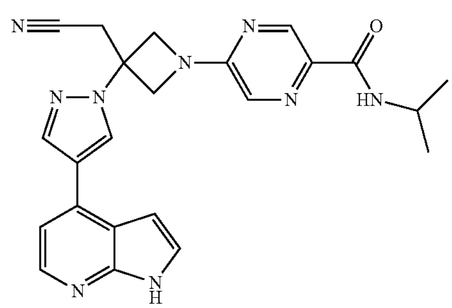 [SMILES: CC(C)NC(=O)c1cnc(N2CC(CC#N)(n3cc(-c4ccnc5[nH]ccc45)cn3)C2)cn1] | + | >10 |
| 18 | US 2013/ 0045963 (Example 45) | {1-(cis-4-{[6-(2-hydroxyethyl)-2-(trifluoromethyl) pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 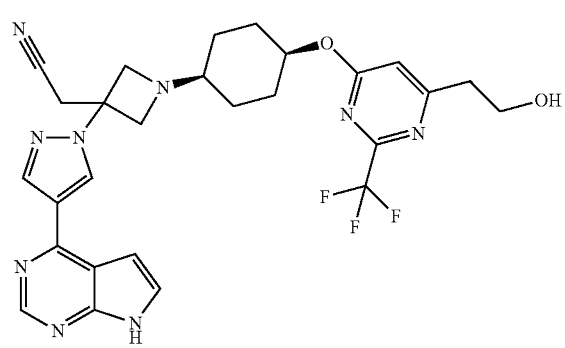 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 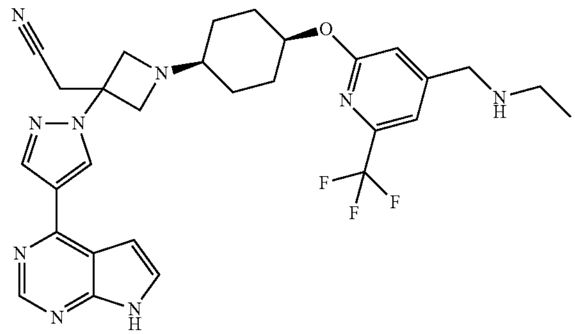 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 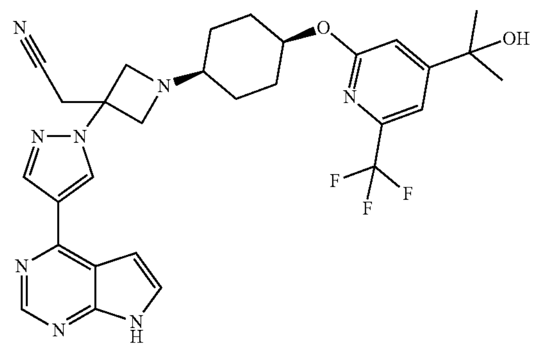 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 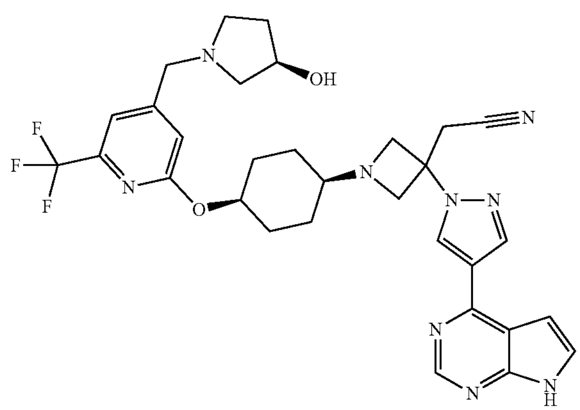 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 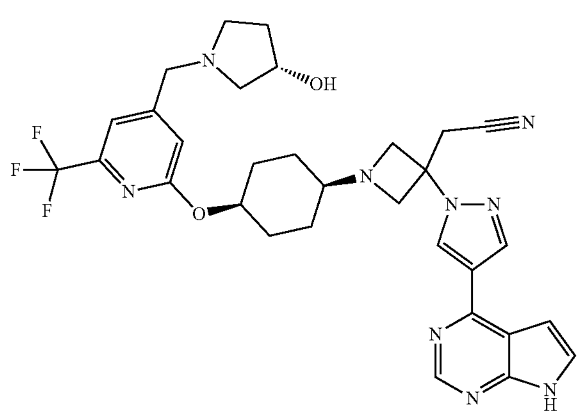 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE 1-continued

| Comp. No. | Prep. | Name | Structure | JAK1 IC$_{50}$ (nM) | JAK2/ JAK1 |
|---|---|---|---|---|---|
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 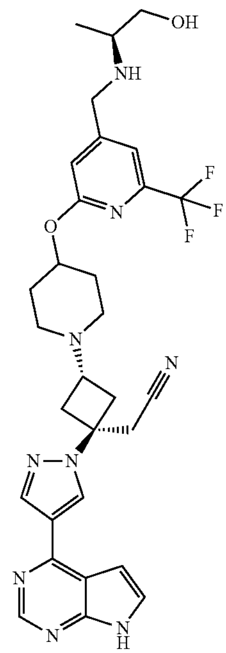 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 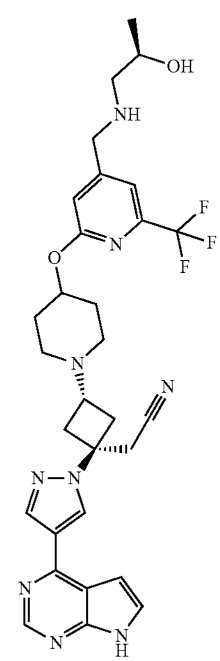 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 25 | US 2014/ 0005166 (Example 15) | {trans-3-(4-{[4-({[(2S)-2-hydroxypropyl] amino}methyl)-6-(trifluoromethyl) pyridin-2-yl]oxy} piperidin-1-yl)-1-[4-(7H-pyrrolo[2,3-d]pyrimidin-4-yl)-1H-pyrazol-1-yl]cyclobutyl} acetonitrile | 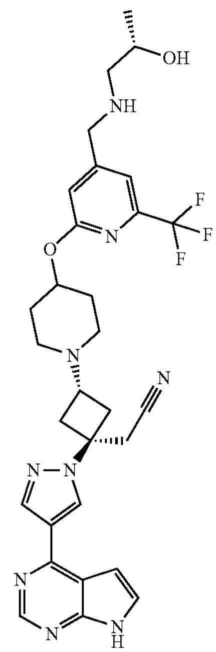 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/ 0005166 (Example 20) | {trans-3-(4-{[4-(2-hydroxyethyl)-6-(trifluoromethyl) pyridin-2-yl]oxy} piperidin-1-yl)-1-[4-(7H-pyrrolo [2,3-d]pyrimidin-4-yl)-1H-pyrazol-1-yl] cyclobutyl} acetonitrile | 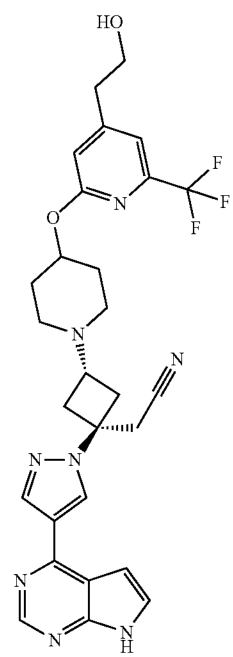 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)

++ means ≤100 nM (see Example A for assay conditions)

+++ means ≤300 nM (see Example A for assay conditions)

[a] Data for enantiomer 1

[b] Data for enantiomer 2

In some embodiments, the JAK1 pathway inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the JAK1 pathway inhibitor is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt.

The synthesis and preparation of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. 2014/0343030, filed May 16, 2014, which is incorporated herein by reference in its entirety.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile monohydrate.

Synthesis of ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, JAK1 pathway inhibitor is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 pathway inhibitor is a compound of Formula I

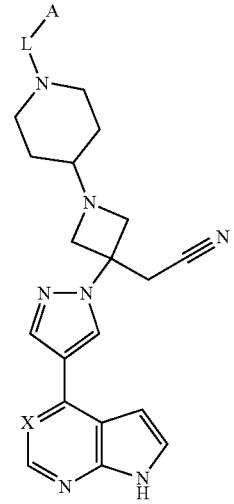

or a pharmaceutically acceptable salt thereof, wherein:

X is N or CH;

L is C(=O) or C(=O)NH;

A is phenyl, pyridinyl, or pyrimidinyl each of which is optionally substituted with 1 or 2 independently selected $R^1$ groups; and each $R^1$ is, independently, fluoro, or trifluoromethyl.

In some embodiments, the compound of Formula I is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the compound of Formula I is 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide, or a pharmaceutically acceptable salt thereof.

In some embodiments, the compound of Formula I is [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile, or a pharmaceutically acceptable salt thereof.

In some embodiments, the JAK1 pathway inhibitor is a compound of Formula II

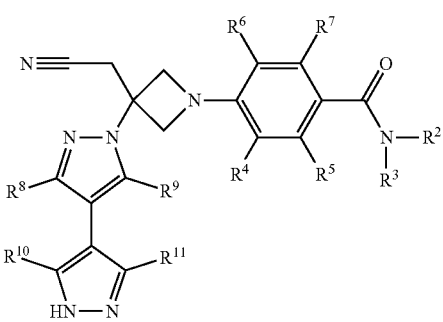

II or a pharmaceutically acceptable salt thereof, wherein:

$R^2$ is $C_{1-6}$ alkyl, $C_{1-6}$ haloalkyl, $C_{3-6}$ cycloalkyl, or $C_{3-6}$ cycloalkyl-$C_{1-3}$ alkyl, wherein said $C_{1-6}$ alkyl, $C_{3-6}$ cycloalkyl, and $C_{3-6}$ cycloalkyl-$C_{1-3}$ alkyl, are each optionally substituted with 1, 2, or 3 substituents independently selected from fluoro, —$CF_3$, and methyl;

$R^3$ is H or methyl;
$R^4$ is H, F, or Cl;
$R^5$ is H or F;
$R^6$ is H or F;
$R^7$ is H or F;
$R^8$ is H or methyl;
$R^9$ is H or methyl;
$R^{10}$ is H or methyl; and
$R^{11}$ is H or methyl.

In some embodiments, the compound of Formula II is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof.

In some embodiments, the JAK1 pathway inhibitor is a compound of Formula III

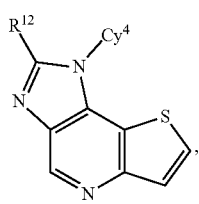

III or a pharmaceutically acceptable salt thereof, wherein:

$Cy^4$ is a tetrahydro-2H-pyran ring, which is optionally substituted with 1 or 2 groups independently selected from CN, OH, F, Cl, $C_{1-3}$ alkyl, $C_{1-3}$ haloalkyl, cyano-$C_{1-3}$ alkyl, HO—$C_{1-3}$ alkyl, amino, $C_{1-3}$ alkylamino, and di($C_{1-3}$ alkyl)amino, wherein said $C_{1-3}$ alkyl and di($C_{1-3}$ alkyl)amino is optionally substituted with 1, 2, or 3 substituents independently selected from F, Cl, $C_{1-3}$ alkylaminosulfonyl, and $C_{1-3}$ alkylsulfonyl; and $R^{12}$ is —$CH_2$—OH, —$CH(CH_3)$—OH, or —$CH_2$—$NHSO_2CH_3$.

In some embodiments, the compound of Formula III is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 pathway inhibitor, or a pharmaceutically acceptable salt thereof, is administered in a daily amount of from about 100 mg to about 600 mg on a free base basis. Accordingly, in some embodiments, the selective JAK1 pathway inhibitor is administered in a daily amount of about 100 mg, about 150 mg, about 200 mg, about 250 mg, about 300 mg, about 350 mg, about 400 mg, about 450 mg, about 500 mg, about 550 mg, or about 600 mg on a free base basis.

In some embodiments, the JAK1 pathway inhibitor, or a pharmaceutically acceptable salt thereof, is administered at a daily amount of about 200 mg on a free base basis.

In some embodiments, the JAK1 pathway inhibitor, or a pharmaceutically acceptable salt thereof, is administered at a daily amount of about 300 mg on a free base basis.

In some embodiments, the JAK1 pathway inhibitor, or a pharmaceutically acceptable salt thereof, is administered at a daily amount of about 400 mg on a free base basis.

In some embodiments, the JAK1 pathway inhibitor, or a pharmaceutically acceptable salt thereof, is administered at a daily amount of about 500 mg on a free base basis.

In some embodiments, the JAK1 pathway inhibitor, or a pharmaceutically acceptable salt thereof, is administered at a daily amount of about 600 mg on a free base basis.

In some embodiments, the JAK1 pathway inhibitor, or a pharmaceutically acceptable salt thereof, is administered once daily at an amount of about 200 mg on a free base basis.

In some embodiments, the JAK1 pathway inhibitor, or a pharmaceutically acceptable salt thereof, is administered once daily at an amount of about 300 mg on a free base basis.

In some embodiments, the JAK1 pathway inhibitor, or a pharmaceutically acceptable salt thereof, is administered once daily at an amount of about 400 mg on a free base basis.

In some embodiments, the JAK1 pathway inhibitor, or a pharmaceutically acceptable salt thereof, is administered once daily at an amount of about 500 mg on a free base basis.

In some embodiments, the JAK1 pathway inhibitor, or a pharmaceutically acceptable salt thereof, is administered once daily at an amount of about 600 mg on a free base basis.

In some embodiments, the JAK1 pathway inhibitor, or a pharmaceutically acceptable salt thereof, is administered as one or more sustained release dosage forms each comprising the JAK1 pathway inhibitor, or a pharmaceutically acceptable salt thereof.

Provided herein is a method for treating a cytokine-related disease or disorder in a subject in need thereof in a subject, comprising administering to the subject a daily dose of from about 100 mg to 600 mg on a free base basis of a JAK1 pathway inhibitor, or a pharmaceutically acceptable salt thereof, wherein the JAK1 pathway inhibitor, or a pharmaceutically acceptable salt thereof, is administered as one or more sustained release dosage forms comprising the JAK1 pathway inhibitor, or a pharmaceutically acceptable salt thereof.

The embodiments described herein are intended to be combined in any suitable combination as if the embodiments are multiply dependent claims (e.g., the embodiments related to the selective JAK1 pathway inhibitor and doses of the same, the embodiments related to any salt forms of the compounds disclosed herein, the embodiments related to the individual types of cytokine related diseases or disorders, and the embodiments related to composition and/or administration can be combined in any combination).

For example, provided herein is a method for treating a cytokine related disease or disorder selected from the group consisting of cytokine release syndrome (CRS), hemophagocytic lymphohistiocytosis (HLH), macrophage activation syndrome (MAS), or CAR-T-cell-related encephalopathy syndrome (CRES), in a subject, the method comprising administering to the subject a once-daily dose of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained-release dosage forms each comprising the {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

Sustained-release dosage forms of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof (Table 1, Compound 1) can be found in US Publ. No. 2015/0065484, filed Aug. 6, 2014, which is hereby incorporated by reference in its entirety.

All possible combinations are not separately listed herein merely for the sake of brevity.

The compounds described herein can be asymmetric (e.g., having one or more stereocenters). All stereoisomers, such as enantiomers and diastereomers, are intended unless otherwise indicated. Compounds that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein can also include isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formulae (I), (II), or (III) or a compound of Table 1 can be optionally substituted with deuterium atoms, such as —$CD_3$ being substituted for —$CH_3$). The term, "compound," as used herein is meant to include all stereoisomers, geometric isomers, tautomers, and isotopes of the structures depicted, unless the name indicates a specific stereoisomer. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "subject", "individual," or "patient," used interchangeably, refers to any animal, including mammals, preferably mice, rats, other rodents, rabbits, dogs, cats, swine, cattle, sheep, horses, or primates, and most preferably humans. In some embodiments, the "subject," "individual," or "patient" is in need of said treatment.

In some embodiments, the inhibitors are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 200 mg, about 1 mg to about 100 mg, about 1 mg to 50 mg, or about 50 mg to about 500 mg. In some embodiments, the dosage of the compound, or a pharmaceutically acceptable salt thereof, is about 200 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease; or (3) preventing the disease, condition or disorder in an individual who may be predisposed to the disease, condition or disorder but does not yet experience or display the pathology or symptomatology of the disease. In some embodiments, treating refers to inhibiting or ameliorating the disease. In some embodiments, treating is preventing the disease.

Combination Therapies

The methods described herein can further comprise administering one or more additional therapeutic agents. The one or more additional therapeutic agents can be administered to a patient simultaneously or sequentially.

In some embodiments, the additional therapeutic agent is an IL-6 antagonist or receptor antagonist. In some embodiments, the IL-6 receptor antagonist is tocilizumab.

In some embodiments, the additional therapeutic agent is an inhibitor of MCP-1. In some embodiments, the additional therapeutic agent is an inhibitor of MIP1B. In some embodiments, the additional therapeutic agent is an inhibitor of IL-2R. In some embodiments, the additional therapeutic agent is an inhibitor of IL-1R. In some embodiments, the additional therapeutic agent is an inhibitor of TNF-α.

In some embodiments, the additional therapeutic agent is an anti-CD25 antibody. In some embodiments, the anti-CD25 antibody is daclizumab.

In some embodiments, the additional therapeutic agent is an antagonist of IL-1β.

In some embodiments, the additional therapeutic agent is an IL1 receptor antagonist (IL1Ra). In some embodiments, the IL1 receptor antagonist (IL1Ra) is anakinra.

In some embodiments, the additional therapeutic agent is a corticosteroid. In some embodiments, the corticosteroid is prednisone.

In some embodiments, any of the preceding additional therapeutic agents is used in further combination with a corticosteroid (e.g., prednisone).

In some embodiments, the additional therapeutic agents comprise tocilizumab and a corticosteroid. In some embodiments, the additional therapeutic agents comprise tocilizumab and prednisone.

Pharmaceutical Formulations and Dosage Forms

When employed as pharmaceuticals, the JAK1 pathway inhibitors or pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the JAK1 pathway inhibitor described herein, or a pharmaceutically acceptable salt thereof, in combination with one or more pharmaceutically acceptable carriers (excipients). In some embodiments, the composition is suitable for topical administration. In making the compositions, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The JAK1 pathway inhibitors may be milled using known milling procedures such as wet milling to obtain a particle size appropriate for tablet formation and for other formulation types. Finely divided (nanoparticulate) preparations of the JAK1 selective inhibitors can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound described herein. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Kits

The present invention also includes pharmaceutical kits useful, for example, in the treatment and/or prevention of cytokine-related diseases or disorders, such as CRS, which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

Example A: In Vitro JAK Kinase Assay

JAK1 pathway inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody takes place for 40 minutes and HTRF signal was measured on a Fusion plate reader (Perkin Elmer, Boston, Mass.). The compounds in Table 1 were tested in this assay and shown to have the $IC_{50}$ values also found in Table 1.

Example B: Anti-CD3 Antibody-Induced Cytokine Release Syndrome in BALB/c Mice

JAK1 pathway inhibitors can be tested for efficacy against CRS according to an in vivo assay described in Ferran, C. et al. *Clin. Exp. Immunol.* 1991, 86, 537-543. Specifically, this study can test the ability of a compound to reduce or ameliorate anti-CD3 antibody-induced cytokine release syndrome (CRS) in BALB/c mice. The antibody, clone 145-2C11, is an immunoglobin G (IgG) hamster MoAb that is specific for the ε chain of the CD3 murine molecule (Léo, O. et al., *Proc. Natl. Acad. Sci. USA*, 1987, 34, 1374). Treatment with 145-2C11 induces high affinity IL-2 receptors at the surface of spleen T-cells and results in a release of some cytokines such as tumor necrosis factor (TNF-α), IL-2, IL-3, IL-6, and interferon-gamma (IFN-γ) (Ferran, et al. *Eur. J. Immunol.* 1990, 20, 509-515 and Algre, M. et al., *Eur. J. Immunol.*, 1990, 707). Release of these cytokines results in behavioral changes (e.g., inactivity, piloerection, etc) of the animals.

A. Materials and Methods

| | |
|---|---|
| Species/strain: | Mice: Male BALB/c |
| Physiological state: | Normal |

| | | | | | | |
|---|---|---|---|---|---|---|
| Group | No. Animals | TA Pre-Treatment (PO) | Dosing schedule | Anti-CD3 (10 µg, IV) | Sacrifice Schedule/Collection | Endpoints |
| 1 | 8/males | Naïve | 60 minutes before anti-CD3 | – | 1.5 hr after anti-CD3 administration Whole blood via cardiac puncture (K$_2$EDTA tubes) | Plasma collection for multiplex cytokine analysis |
| 2 | 8/males | Vehicle | | + | | |
| 3 | 8/males | Compound 1 (60 mg/kg) | | + | | |
| 4 | 8/males | Compound 1 (120 mg/kg) | | + | | |

TABLE 1A

Study Design

-continued

| | |
|---|---|
| Age/weight range at start of study: | 6-8 weeks old |
| Animal supplier: | Charles River Laboratories |
| Number/sex of animals: | 32 total Male mice |
| Randomization: | Mice will be randomized into four (4) groups of eight (8) mice prior to the commencement of the study. |
| Justification: | Injection of anti-CD3 antibody (clone 145-2C11) has been shown in the literature to induce cytokine release syndrome and serves as a model with which to test the efficacy of potential therapies. |
| Replacement | Animals will not be replaced during the course of the study. |

Anti-CD3ε

| | |
|---|---|
| Identity and lot number: | Anti-CD3ε Clone 145-2C11 |
| Source: | BioXCell |
| Storage conditions: | 4° C. |
| Vehicle: | Sterile saline |
| Dose: | 10 µg |
| Dosing Route/Volume | IV, 100 µL per animal |
| Compound: | Compound 1 (Jak1 inhibitor)[4] |
| Storage conditions: | RT (formulation RT on tube rotator) |
| Vehicle: | 0.5% Methylcellulose |
| Dose(s): | 60 mg/kg and 120 mg/kg |
| Dosing Route/Volume | PO, 0.1 mL/20 g (5 mL/kg) |
| Frequency and duration of dosing: | QD on day 0 |

[4] The synthesis and preparation of Compound 1 of Table 1 or {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in U.S. patent Pub. No. 2011/0224190, filed Mar. 9, 2011, U.S. patent Pub. No. 2013/0060026, filed Sep. 6, 2012, and U.S. patent Pub. No. 2014/0256941, filed Mar. 5, 2014, each of which is incorporated herein by reference in its entirety.

B. Experimental Design

The main objective of this study was to test the ability of a JAK1 pathway inhibitor (e.g., Compound 1) to reduce or ameliorate anti-CD3 antibody-induced cytokine release syndrome (CRS) in BALB/c mice. A total of thirty-two (32) BALB/c mice were used for this one day study. Animals were weighed prior to test article dosing, and monitored for the duration of the experiment. On day 0, one hour (1) prior to anti-CD3 antibody administration, vehicle (0.5% methylcellulose) or Compound 1 were given in a single dose via oral gavage (PO) to animals in groups 2-4 as is detailed in Table 1A. Group 1 served as naïve controls and were not treated. Following the 1 hour pre-treatment with vehicle or Compound 1, animals in Groups 2-4 were administered 10 µg of an anti-CD3ε antibody (clone 145-2C11) via intravenous injection (IV) in order to induce CRS. All animals were euthanized via $CO_2$ inhalation 1.5 hours after anti-CD3 administration. Whole blood was collected via cardiac puncture into $K_2$EDTA tubes and stored on ice until plasma processing occurred. Plasma was collected and stored at −80° C. until cytokine multiplex was performed.

C. Experimental Procedures

I. Test Article Pre-Treatment

On day 0, animals were dosed with vehicle or test articles or Compound 1 as shown in Table 1A. Group 2 received a single dose of vehicle (0.5% methylcellulose) via PO at 0.1 mL/20 g. Group 3 received a single dose of 60 mg/kg Compound 1 via PO at 0.1 mL/20 g. Group 4 received a single dose of 120 mg/kg Compound 1 via PO at 0.1 mL/20 g. Group 1 served as the naïve controls and were not treated.

II. Anti-CD3ε Antibody Administration

One (1) hour after test article administration, an anti-CD3ε antibody (clone 145-2C11) was administered via IV injection to Groups 2-4. Each animal in Groups 2-4 received 10 µg of anti-CD3ε antibody in 0.1 mL.

III. In-Life Monitoring

After the administration of the anti-CD3 antibody, animals were closely monitored for signs of distress due to the resulting systemic inflammatory response. Animals that were unable to right themselves, cold to the touch, or moribund were euthanized. Moribund animals were euthanized by $CO_2$ inhalation, and blood was collected via cardiac puncture and plasma retained.

IV. Sacrifice

One and a half (1.5) hours after anti-CD3 antibody administration all animals were euthanized by $CO_2$ inhalation.

V. Collection of Samples

Upon sacrifice, whole blood was collected from each animal via cardiac puncture into $K_2$EDTA tubes. The blood was centrifuged and the plasma collected in cryovials. The plasma was frozen and stored at −80° C. for the downstream cytokine multiplex assay.

VI. Cytokine Multiplex Analysis

Plasma samples are thawed on ice and used for a cytokine multiplex according to the manufacturer's protocol (ThermoFisher).

D. Results

Figure 1:
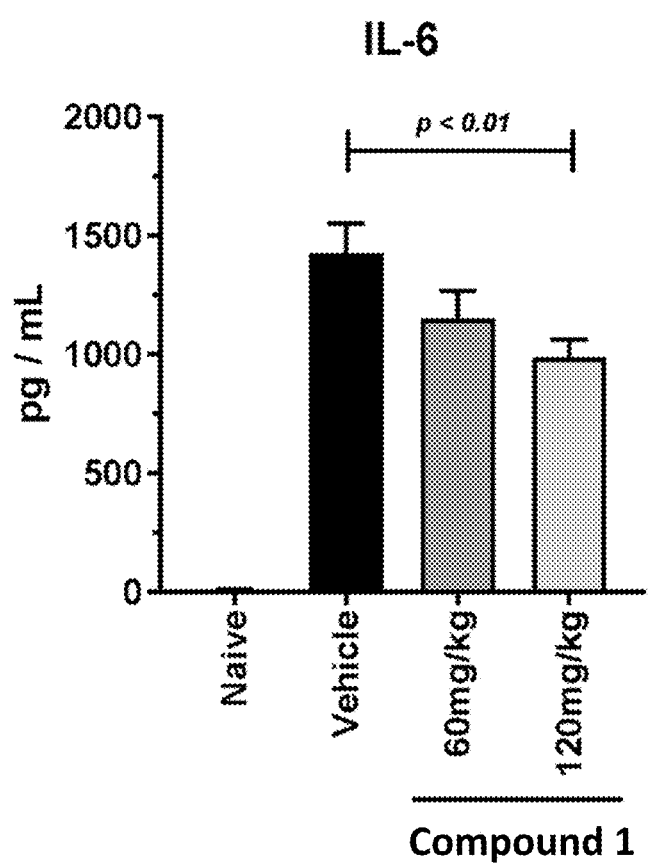
FIG. 1 depicts dose-dependent inhibition of the IL-6 concentrations upon administration of Compound 1 within the blood compartment during anti-CD3 antibody induced cytokine release syndrome (see Example B).

Compound 1 dose-dependently inhibited IL-6 concentrations within the blood compartment (FIG. 1). This serves as confirmation of the biological activity observed in the Con A preclinical model described below in Example C. An unpaired one-way analysis of variance (ANOVA) incorporating Sidak's multiple test comparison was performed using GraphPad Prism (version 4.00; GraphPad Software, San Diego Calif., USA). A value of $p<0.05$ was considered significant.

Example C: Concanavalin A Induced Cytokine Release Syndrome

Concanavalin A (Con A) is a selective T lymphocyte mitogen resulting in broad inflammatory cytokine release and proliferation of CD4 and CD8 T-cells. Injection of Con-A has been shown in the literature to induce cytokine release syndrome and serves as a model with which to test the efficacy of cytokine release syndrome therapies (Gantner, F. at al. *Hepatology*, 1995, 21, 190-198). The mitogen response is dependent on expression of the T-cell receptor. Animals exhibit behavioral changes such as fever, malaise, hypotension, hypoxia, capillary leak, and potential multi-organ toxicity.

A. Materials and Methods

| | |
|---|---|
| Species/strain: | Mice: Female BALB/c |
| Physiological state: | Normal |
| Age/weight range at start of study: | 6-8 weeks old |
| Animal supplier: | Taconic |
| Number/sex of animals: | 40 total mice |
| Randomization: | Mice were randomized into five (5) groups of eight (8) mice prior to the commencement of the study. |
| Justification: | Injection of Con-A has been shown in the literature to induce cytokine release syndrome and serves as a model with which to test the efficacy of potential therapies. |

B. Experimental Design

In particular, this study tests the ability of a selective JAK1 inhibitor (e.g., Compound 1, Table 1) to reduce or ameliorate Con A-induced cytokine release syndrome (CRS) in BALB/c mice. A total of forty (40) BALB/c mice were used for this one day study. Animals were weighed prior to test article dosing, and monitored for the duration of the experiment. On day 0, Sixty (60) minutes prior to Con A administration, vehicle (0.5% methylcellulose) or Compound 1 (60 and 120 mg/kg) was given in a single dose via oral gavage (PO) to animals in groups 2-4 as detailed in Table 2A. Group 1 served as naïve controls and were not treated. Following the 45 minutes pre-treatment with vehicle or Compound 1, animals in Groups 2-4 were administered 20 mg/kg of Con A via intravenous injection (IV) in order to induce CRS. All animals were euthanized via $CO_2$ inhalation two hours after Con A administration. Whole blood was collected via cardiac puncture into $K_2$EDTA tubes and stored on ice until plasma processing occurs. Plasma was collected and stored at −80° C. until cytokine multiplex was performed.

C. Experimental Procedures

Day −1

Animals were weighed and Con-A dose (20 mg/kg) calculated.

Vehicle and Compound 1 were prepared at corresponding doses.

Day 0

I. Test Article Pre-Treatment

On day 0, animals were dosed with vehicle or Compound 1, as in Table 2A. Group 1 served as the naïve controls and were not treated. Group 2 received a single dose of vehicle (0.5% methylcellulose) via PO at 0.1 mL/20 g. Group 3 received a single dose of 60 mg/kg Compound 1 via PO at 0.1 mL/20 g. Group 4 received a single dose of 120 mg/kg Compound 1 via PO at 0.1 mL/20 g.

II. Con-A Administration

Sixty (60) minutes after test article administration, Con-A was administered via IV injection to Groups 2-4. Each animal in Groups 2-4 received 20 mg/kg of Con-A in 0.2 mL.

III. In-Life Monitoring

After the administration of Con-A, animals were closely monitored for signs of distress due to the resulting systemic inflammatory response.

IV. Sacrifice

Two hours after Con-A administration all animals were euthanized by $CO_2$ inhalation.

V. Collection of Samples

Upon sacrifice, whole blood was collected from each animal via cardiac puncture into $K_2$EDTA tubes. The blood was centrifuged and the plasma collected in cryovials. The plasma was frozen and stored at −80° C. for the downstream cytokine multiplex assay.

VI. Cytokine Multiplex Analysis

Plasma samples are thawed on ice and used for a cytokine multiplex according to the manufacturer's protocol (ThermoFisher).

D. Results

Figure 2A:
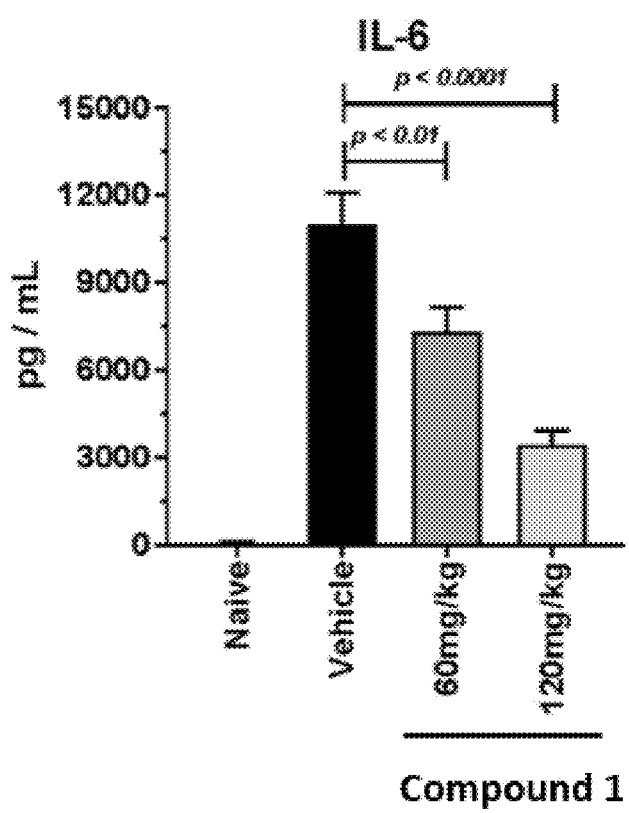
FIGS. 2A-2C depict dose dependent inhibition of T-cell derived cytokines (i.e., IL-6, IFNγ, and GM-CSF) upon administration of Compound 1 during concanavalin A induced cytokine release syndrome (see Example C).
Figure 2B:
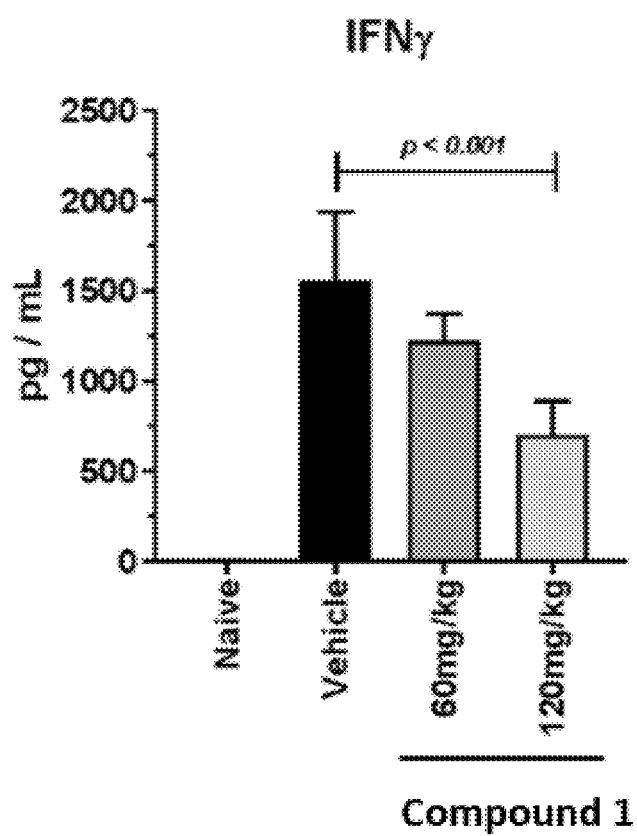
Figure 2C:
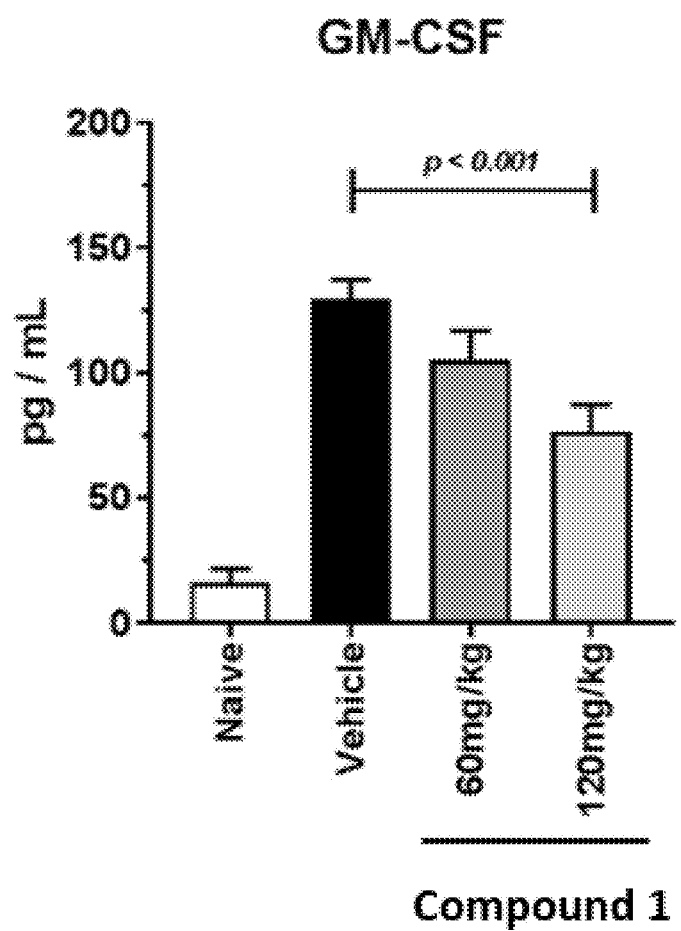
Figure 3A:
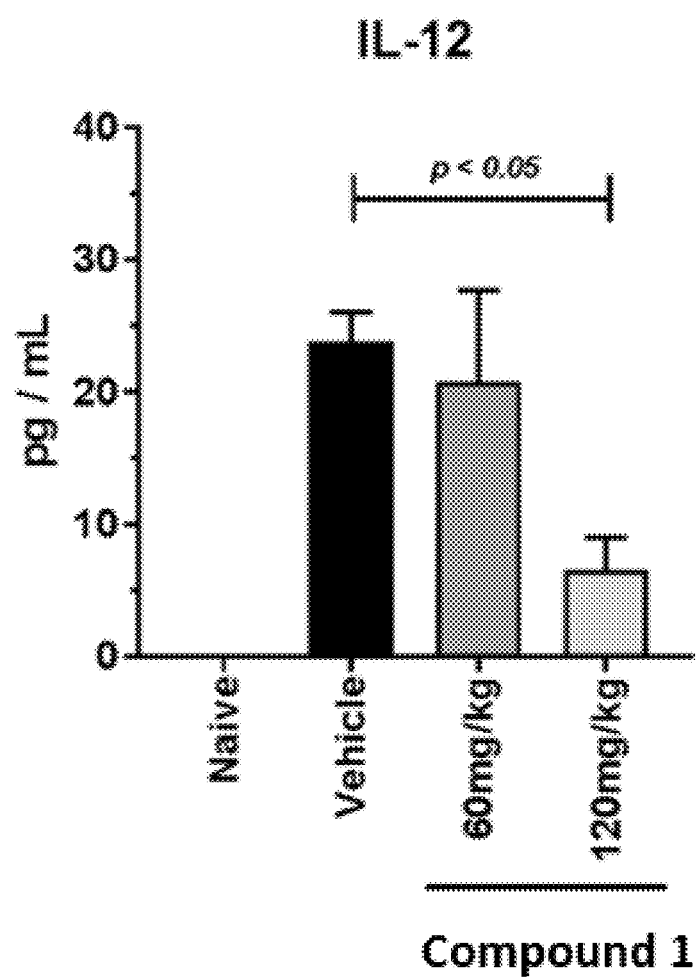
FIGS. 3A-3C depict dose dependent inhibition of monocyte and/or macrophage derived cytokines (i.e., IL-12, IL-1β, and IL-18) upon administration of Compound 1 during concanavalin A induced cytokine release syndrome (see Example C).
Figure 3B:
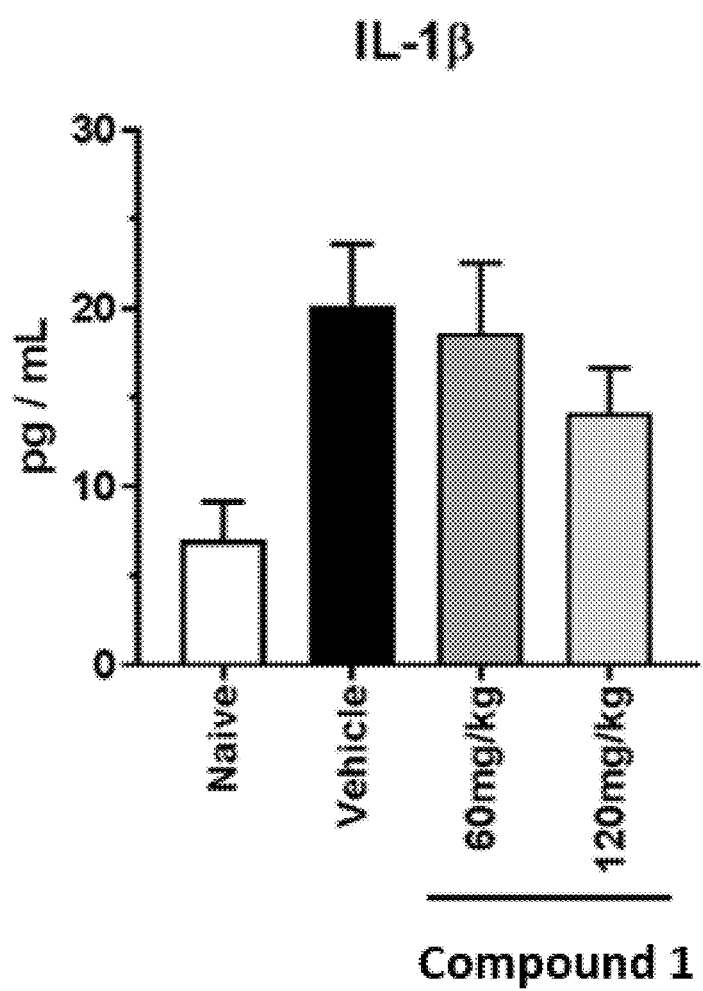
Figure 3C:
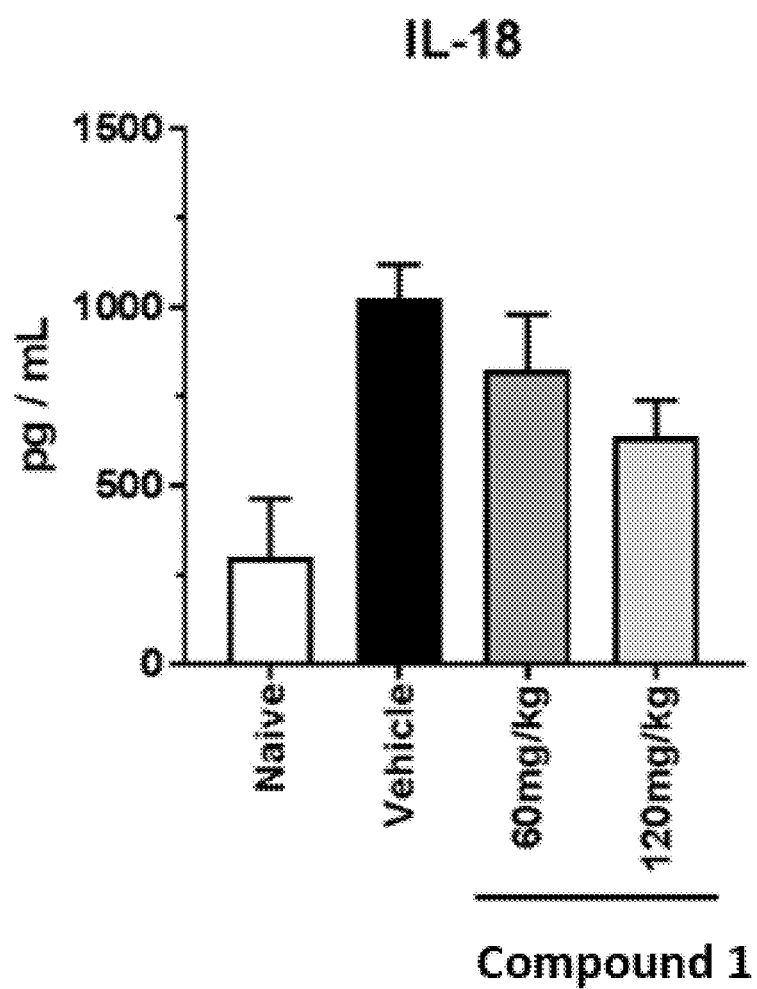

Compound 1 dose-dependently inhibited IL-6 concentrations within the blood compartment (FIG. 2A). This cytokine is a key mediated of CRS pathophysiology. The T-cell derived IFNγ and GM-CSF cytokines were also significantly inhibited suggesting that Compound 1 has therapeutic potential beyond tocilizumab's restricted mechanism of action (anti-IL-6R only) (FIGS. 2B and 2C).

Monocytes and/or macrophage derived cytokines were also reduced. Statistically significant dose-dependent IL-12 reduction (FIG. 3A) was observed as well as trends for treatment effect with IL-1β (FIG. 3B) and IL-18 (FIG. 3C) suggesting that JAK1 specific inhibition has therapeutic potential across immune cell types implicated in CRS pathology.

TABLE 2A

Study Design

| Group | No. of Animals | Pre-Treatment (PO) | Dosing schedule | Con-A (IV) | Sacrifice Schedule/Collection | Endpoints |
|---|---|---|---|---|---|---|
| 1 | 10 | Naïve | 60 minutes before Con A | − | 2 h after Con A administration | Plasma collection for multiplex cytokine analysis |
| 2 | 10 | Vehicle | | + | Whole blood via cardiac puncture | |
| 3 | 10 | Compound 1 (60 mg/kg) | | + | | |
| 4 | 10 | Compound 1 (120 mg/kg) | | | | |

Importantly, the cytokine IL-5 (FIG. 4) was unaffected by Compound 1 treatment, is JAK1 independent and not implicated in CRS pathology. This data suggests that Compound 1 based efficacy is not mediated via broad, non-specific, immune suppression.

An unpaired one-way analysis of variance (ANOVA) incorporating Sidak's multiple test comparison was performed using GraphPad Prism (version 4.00; GraphPad Software, San Diego Calif., USA). A value of $p<0.05$ was considered significant.

Example D: Preparation of Sustained Release Formulations of Compound 1

Sustained release tablets comprising Compound 1 were prepared with the excipients being in the amounts shown in the tables below. Protocol A was used for the SR1 tablets, Protocol B was used for the SR2 tablets, Protocol C was used for the SR3 tablets and the 25 mg SR tablets, and Protocol D was used for the SR4 tablets. These procedures are disclosed in US Patent Publ. No. 2015/0065484, which is directed to sustained release dosage forms of Compound 1.

Protocol A:
Step 1. Individually screen the adipic acid salt of Compound 1, microcrystalline cellulose, hypromelloses (Methocel K100 LV and Methocel K4M), and lactose monohydrate.
Step 2. Transfer the screened material from Step 1 to a suitable blender and mix.
Step 3. Transfer the blend from Step 2 to a suitable granulator and mix.
Step 4. Add purified water while mixing.
Step 5. Transfer the granules from Step 4 into a suitable dryer and dry until LOD is less than 3%.
Step 6. Screen the granules from Step 5.
Step 7. Mix screened Magnesium Stearate with granules in Step 6 in a suitable blender.
Step 8. Compress the final blend in Step 7 on a suitable rotary tablet press.

Protocol B:
Step 1. Individually screen the adipic acid salt of Compound 1, microcrystalline cellulose, hypromellose and pregelatinized starch.
Step 2. Transfer the screened material from Step 1 to a suitable blender and mix.
Step 3. Transfer the blend from Step 2 to a suitable granulator and mix.
Step 4. Add purified water while mixing.
Step 5. Transfer the granules from Step 4 into a suitable dryer and dry until LOD is less than 3%.
Step 6. Screen the granules from Step 5.
Step 7. Individually screened polyox, butylated hydroxytoluene and colloidal silicone dioxide.
Step 8. Transfer the granules from Step 6 and material from Step 7 into a suitable blender and mix.
Step 9. Add screened Magnesium Stearate to the material in Step 8 and continue blending.
Step 10. Compress the final blend in Step 9 on a suitable rotary tablet press.

Protocol C:
Step 1. Individually screen lactose monohydrate, the adipic acid salt of Compound 1, microcrystalline cellulose and hypromelloses through a suitable screen.
Step 2. Transfer the screened material from Step 1 to a suitable blender and mix.
Step 3. Transfer the blend from Step 2 to a suitable granulator and mix.
Step 4. Add purified water while mixing.
Step 5. Screen wet granules through a suitable screen.
Step 6. Transfer the granules from Step 5 into a suitable dryer and dry until LOD is less than 3%.
Step 7. Mill the granules from Step 6.
Step 8. Mix screened magnesium stearate with granules in Step 7 in a suitable blender.
Step 9. Compress the final blend in Step 8 on a suitable rotary tablet press.

Protocol D:
Step 1. Individually screen pregelatinized starch, the adipic acid salt of Compound 1, hypromellose, and a portion of required microcrystalline cellulose through a suitable screen.
Step 2. Transfer the screened material from Step 1 to a suitable blender and mix.
Step 3. Transfer the blend from Step 2 to a suitable granulator and mix.
Step 4. Add purified water while mixing.
Step 5. Screen wet granules through a suitable screen.
Step 6. Transfer the granules from Step 5 into a suitable dryer and dry until LOD is less than 3%.
Step 7. Mill the granules from Step 6.
Step 8. Screen the remaining portion of microcrystalline cellulose and half of the sodium bicarbonate.
Step 9. Transfer the milled granules from Step 7 and screened materials from Step 8 into a suitable blender and mix.
Step 10. Screen the remaining portion of sodium bicarbonate and mix with blend in Step 9.
Step 11. Screen magnesium stearate and mix with blend in Step 10.
Step 12. Compress the final blend in Step 11 on a suitable rotary tablet press.

SR1: Composition of 100 mg Sustained Release Tablets

| Component | Function | Weight (mg/tablet) | Composition (wt %) |
|---|---|---|---|
| Adipic acid salt of Compound 1 [a] | Active | 126.42 [a] | 21.1 |
| Microcrystalline Cellulose | Filler | 60.0 | 10.0 |
| Hypromellose (Methocel K100LV) | Release Control | 60.0 | 10.0 |
| Hypromellose (Methocel K4M) | Release Control | 60.0 | 10.0 |
| Lactose Monohydrate | Filler | 290.58 | 48.4 |
| Magnesium Stearate [b] | Lubricant | 3.0 | 0.5 |
| Purified Water [c] | Granulating Liquid | q.s. | — |
| Total | | 600.0 | 100 |

[a] Conversion factor for adipate salt to free base is 0.7911
[b] Added after granulation
[c] Removed during processing SR2: Composition of 100 mg Sustained Release Tablets

| Component | Function | Weight (mg/tablet) | Composition (wt %) |
|---|---|---|---|
| Adipic acid salt of Compound 1 [a] | Active | 126.4 [a] | 21.1 |
| Microcrystalline Cellulose | Filler | 180.0 | 30.0 |

-continued

| Component | Function | Weight (mg/tablet) | Composition (wt %) |
|---|---|---|---|
| Hypromellose (Methocel K100LV) | Binder | 6.0 | 1.0 |
| Polyethylene Oxide (Polyox WRS 1105) [b] | Release Control | 180.0 | 30.0 |
| Pregelatinized Starch | Filler | 101.6 | 16.9 |
| Colloidal Silicon Dioxide [b] | Glidant | 3.0 | 0.5 |
| Butylated Hydroxytoluene [b] | Antioxidant | 0.012 | 0.002 |
| Magnesium Stearate [b] | Lubricant | 3.0 | 0.5 |
| Purified Water [c] | Granulating Liquid | q.s. | — |
| Total | | 600.0 | 100.0 |

[a] Conversion factor for adipate salt to free base is 0.7911
[b] Added after granulation
[c] Removed during processing SR3 (100 mg): Composition of 100 mg Sustained Release Tablets

| Component | Function | Weight (mg/tablet) | Composition (wt %) |
|---|---|---|---|
| Adipic acid salt of Compound 1 [a] | Active | 126.4 [a] | 21.1 |
| Microcrystalline Cellulose | Filler | 108.0 | 18.0 |
| Hypromellose (Methocel K100LV) | Release Control | 42.0 | 7.0 |
| Hypromellose (Methocel K4M) | Release Control | 30.0 | 5.0 |
| Lactose Monohydrate | Filler | 290.6 | 48.4 |
| Magnesium Stearate [b] | Lubricant | 3.0 | 0.5 |
| Purified Water [c] | Granulating Liquid | q.s. | — |
| Total | | 600.0 | 100.0 |

[a] Conversion factor for adipate salt to free base is 0.7911
[b] Added after granulation
[c] Removed during processing SR4: Composition of 100 mg Sustained Release Tablets

| Excipient | Function | Weight (mg/tablet) | Composition (wt %) |
|---|---|---|---|
| Adipic acid salt of Compound 1 [a] | Active | 126.4 [a] | 21.1 |
| Microcrystalline Cellulose [d] | Filler | 104.6 | 17.4 |
| Hypromellose (Methocel K100LV) | Release Control | 210.0 | 35.0 |
| Pregelatinized Starch | Filler | 60.0 | 10.0 |
| Sodium Bicarbonate [b] | Gastric Floating Aid | 96.0 | 16.0 |
| Magnesium Stearate [b] | Lubricant | 3.0 | 0.5 |
| Purified Water [c] | Granulation Liquid | q.s. | — |
| Total | | 600.0 | 100.0 |

[a] Conversion factor for adipate salt to free base is 0.7911
[b] Added after granulation
[c] Removed during processing
[d] Partial added before and partial added after granulation 25 mg SR: Composition of 25 mg Sustained Release Tablets

| Component | Function | Weight (mg/tablet) | Composition (wt %) |
|---|---|---|---|
| Adipic acid salt of Compound 1 [a] | Active | 31.6 [a] | 12.6 |
| Microcrystalline Cellulose | Filler | 105.0 | 42.0 |
| Hypromellose, (Methocel K100LV) | Release Control | 25.0 | 10.0 |
| Hypromellose, (Methocel K4M) | Release Control | 25.0 | 10.0 |
| Lactose Monohydrate | Filler | 62.15 | 24.9 |
| Magnesium Stearate [b] | Lubricant | 1.25 | 0.5 |
| Purified Water [c] | Granulating Liquid | q.s. | — |
| Total | | 250 | 100.0 |

[a] Conversion factor for adipate salt to free base is 0.7911
[b] Added after granulation
[c] Removed during processing Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method for treating cytokine release syndrome in a subject, said method comprising administering to the subject a JAK1 selective pathway inhibitor which is {1-{1-[3-fluoro-2 -(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile, or a pharmaceutically acceptable salt thereof.

2. The method of claim 1, wherein the JAK1 selective pathway inhibitor is {1-{1-[3-fluoro-2-(trifluoromethyl) isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

3. The method of claim 1, further comprising administering tocilizumab to said subject.

4. The method of claim 1, further comprising administering a corticosteroid to said subject.

5. The method of claim 1, further comprising administering prednisone to said subject.

6. The method of claim 1, further comprising administering tocilizumab and a corticosteroid to said subject.

7. The method of claim 3, wherein the JAK1 selective pathway inhibitor is {1-{1-[3-fluoro-2-(trifluoromethyl) sonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

8. The method of claim 4, wherein the JAK1 selective pathway inhibitor is {1-{1-[3 -fluoro-2-(trifluoromethyl) isonicotinoyl]piperidin-4-yl}-3 [4-(7H-pyrrolo[2,3-d]pyrimidin-4-yl)-1H-pyrazol-1-yl]azetidin-3-yl}acetonitrile adipic acid salt.

9. The method of claim 5, wherein the JAK1 selective pathway inhibitor is {1-{1-[3 -fluoro-2-(trifluoromethyl) isonicotinoyl]piperidin-4-yl}-3[4-(7H-pyrrolo[2,3-d]pyrimidin-4-y1)-1H-pyrazol-1-yl]azetidin-3-yl}acetonitrile adipic acid salt.

10. The method of claim 6, wherein the JAK1 selective pathway inhibitor is {1-{1-[3-fluoro-2-(trifluoromethyl)

isonicotinoyl]piperidin-4-yl}-3 [4-(7H-pyrrolo[2,3-d]pyrimidin-4-yl)-1H-pyrazol-1-yl]azetidin-3-yl}acetonitrile adipic acid salt.

11. The method of claim 1, wherein the treating comprises ameliorating or inhibiting cytokine release syndrome in the subject.

12. A method for treating cytokine release syndrome in a subject, said method comprising administering to the subject a monotherapy which is {1-{1-[3-fluoro-2-(trifluoromethyl)isonicotinoyl]piperidin-4-yl}-3 [4-(7H-pyrrolo[2,3-d]pyrimidin-4-yl)-1H-pyrazol-1-yl]azetidin-3-yl}acetonitrile, or a pharmaceutically acceptable salt thereof.

13. The method of claim 12, wherein the treating comprises ameliorating or inhibiting cytokine release syndrome in the subject.

14. A method for treating cytokine release syndrome in a subject, said method comprising administering to the subject a monotherapy which is {1-{1[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt.

15. The method of claim 14, wherein the treating comprises ameliorating or inhibiting cytokine release syndrome in the subject.

\* \* \* \* \*